United States Patent [19]

Aldridge et al.

[11] 4,173,515
[45] Nov. 6, 1979

[54] GROUP D ENTEROCOCCI BROTH

[75] Inventors: Clifton Aldridge, Crawford County; Sandra F. Gibson, Chesterfield, both of Mo.; Richard D. Vannest, Richardson, Tex.; Gregory D. Rodgers, Florissant, Mo.

[73] Assignee: McDonnell Douglas Corporation, St. Louis, Mo.

[21] Appl. No.: 792,715

[22] Filed: May 2, 1977

Related U.S. Application Data

[63] Continuation-in-part of Ser. No. 682,661, May 3, 1976, abandoned.

[51] Int. Cl.² .............................................. C12K 1/10
[52] U.S. Cl. ..................................................... 435/38

[56] References Cited

PUBLICATIONS

Robert Bailey and Elvyn Scott, Diagnostic Microbiology; 2nd ed. the C.V. Mosby Company; 1966; pp. 26, 295 and 296.

*Primary Examiner*—Raymond N. Jones
*Assistant Examiner*—Robert J. Warden

[57] ABSTRACT

A broth medium for the detection of Group D enterococci in urine. The medium employs neomycin sulfate to inhibit growth of *Staphylococcus aureus*, potassium tellurite to inhibit growth of gram-negative organisms, and ferric ammonium citrate and esculin hydrolysate indicators.

9 Claims, No Drawings

GROUP D ENTEROCOCCI BROTH

REFERENCE TO OTHER APPLICATION

This application is a continuation-in-part of our prior copending application Ser. No. 682,661 filed May 3, 1976 now abandoned, entitled STREPTOCOCCUS FAECALIS BROTH.

BACKGROUND OF THE INVENTION

Group D enterococci such as *Streptococcus faecalis*, are microorganisms which occur in urine and feces of man and other animals. The presence of these microorganisms in water supplies is a reliable indicator of fecal or sewage pollution. If *Streptococcus faecalis* is present in a given sample of water or urine, it is also possible that *E. Coli*, Proteus, and other like organisms are also present.

The medium of this invention is an improved medium designed for use with the optical detection system disclosed in U.S. applications Ser. No. 255,533 filed May 22, 1972 now abandoned and 461,249 filed Apr. 16, 1974 now U.S. Pat. No. 3,963,355, and in the improved devices disclosed and claimed in applications filed on May 3, 1976 by Charles, Jones, Staples, and Wiegner entitled AUTOMATED MICROBIAL ANALYZER Ser. No. 682,664 now U.S. Pat. No. 4,118,280 and MACHINE AND PROCESS FOR READING CARDS CONTAINING MEDICAL SPECIMENS Ser. No. 682,728 now U.S. Pat. No. 4,116,775. These applications describe mechanism and apparatus suitable for analyzing specimens for specific microorganisms using a plastic tray or card which contains a series of dried culture media contained in separate but connected cells, each of the media being specific to a single organism. When the sample is inserted into the card, mixed with the media in the cells, and incubated in the machine, the organism (or organisms) present in the specimen interacts with the culture medium specific to that organism and produces a change in the medium which is read by the machine to indicate the presence of that organism. The change in the medium involves a change in the light transmitting properties of the medium, i.e., a color change or change in turbidity. The change may be caused by metabolic activity of the organism, which, for example, may cause production of acid and a change in pH which causes a color change in a pH sensitive indicator in the medium. The change in the light transmitting properties of the medium also could be caused by a precipitate forming in the medium due to metabolic activity of the organism or it could be caused by growth of the organism.

The specific media designed for use in the aforesaid cards are all designed to favor growth of one microorganism and to inhibit growth of other organisms, are capable of being freeze dried, and can function in the low $O_2$ environment of the wells of the card described in detail in said copending applications AUTOMATED MICROBIAL ANALYZER and MACHINE AND PROCESS FOR READING CARDS CONTAINING MEDICAL SPECIMENS.

We have discovered a medium which can selectively identify Group D enterococci organisms in urine when the medium is placed in the wells of the cards described in application AUTOMATED MICROBIAL ANALYZER.

Positive results are indicated by means of a precipitate forming in the medium, which causes a change in the light transmitting character of the medium, which change is read by the mechanism described in application AUTOMATED MICROBIAL ANALYZER. The entire test can be completed within 12–18 hours, whereas current methods of detection require from about 36 to about 48 hours.

SUMMARY OF THE INVENTION

This invention involves a broth medium for the detection of Group D enterococci in urine.

The medium contains Phytone, Trypticase, esculin hydrolysate, neomycin sulfate, potassium tellurite, and an indicator which shows the presence of Group D enterococci by means of precipitation.

A novel feature of the invention lies in the use of neomycin sulfate which operates to inhibit growth of *Staphylococcus aureus*, and potassium tellurite which operates to inhibit growth of gram-negative organisms.

DETAILED DESCRIPTION

The detection broth of the present invention contains from about 27 to about 33 g/l nutrients, about 0.48 to about 0.52 g/l of an indicator which indicates the presence of Group D enterococci organisms, about 9800 mg/l to about 10,200 mg/l neomycin sulfate which operates as a biological inhibitor to inhibit the growth of *Staphylococcus aureus* which normally gives positive results in tests for Group D enterococci specifically *Streptococcus faecalis*, and about 0.98 to about 1.02 ml/l potassium tellurite (1% stock solution) which operates to inhibit growth of gram-negative organisms.

The nutrient portion of the medium contains from about 13.5 to about 16.5 gm/l Trypticase Peptone from BBL, from about 4.5 to about 5.5 gm/l Phytone Peptone from BBL, and from about 0.9 to about 1.1 gm/l esculin hydrolysate.

Trypticase is a peptone derived from casein by pancreatic digestion.

Phytone is a peptone formed by the papaic digestion of soy meal and is high in vitamins, especially thiamine.

Suitable substitutes for Trypticase and Phytone are any of the peptones conventionally used in nutrient broths.

The purpose of the peptones are to promote growth of the Group D enterococci organisms.

A suitable biological pH indicator is ferric ammonium citrate. This indicator is used because it allows detection of Group D enterococci by the mechanism described in application AUTOMATED MICROBIAL ANALYZER by means of precipitate formation, thus changing the light transmitting characteristics of the medium.

When esculin hydrolysate is acted upon by *Streptococcus faecalis* and other Group D enterococci, a substance called esculetin is released. This esculetin reacts with the ferric ion of the indicator to form the precipitate that indicates the presence of Group D enterococci.

Sodium thioglycollate is used to reduce the amount of available oxygen in the medium. This reduction of oxygen promotes growth of Group D enterococci, thus resulting in an accelerated time of detection.

Sodium hydroxide is used to adjust the pH of the medium to about 6.6.

An important aspect of this invention lies in the action of the chemical inhibitors, neomycin sulfate, and potassium tellurite. These inhibitors act to inhibit the growth of organisms other than Group D enterococci.

Growth of species of *Staphylococcus aureus*, gram-negative organisms and organisms which result in high yields of positives by conventional detection methods is inhibited by these chemical inhibitors in the process.

The concentration of neomycin sulfate can be from about 9800 to about 10,200 mg/l, and it is most effective at 10,000 mg/l.

The concentration of potassium tellurite (1% stock solution) can be from about 0.98 ml/l to about 1.02 ml/l, and it is most effective at 1.0 ml/l.

If the concentration of any inhibitor is too low, a higher yield of unwanted false positives occurs. If the concentration is too high, a lower yield of positives occurs.

EXAMPLE I

To prepare a 2× medium in an amount of 100 ml, the Group D enterococci detection broth is prepared by thoroughly mixing the following components in the specified amounts.

| | |
|---|---|
| Trypticase | 3.0 gm |
| Phytone | 1.0 gm |
| Esculin hydrolysate | 0.2 gm |
| Sodium thioglycollate | 0.4 gm |
| Neomycin sulfate | 2000. mgm |
| Potassium tellurite (1% stock solution) | 0.2 ml |
| Ferric Ammonium Citrate | 0.1 gm |
| Distilled water to 100 ml | |

The pH of the medium is adjusted to 6.6 by means of hydrochloric acid.

What is claimed is:

1. A broth medium for the detection of Group D enterococci in polymicrobic specimen comprising:
    (a) a nitrogen source,
    (b) a carbon source,
    (c) an antibiotic inhibitor to inhibit growth of *Staphylococcus aureus*,
    (d) an inhibitor to inhibit growth of gram-negative organisms, and
    (e) an indicator system which comprises ferric ammonium citrate and esculin hydrolysate whereby metabolic activity of Group D enterococci forms a precipitate in the medium.

2. The medium of claim 1 wherein the antibiotic inhibitor is neomycin sulfate.

3. The medium of claim 1 wherein about 9800 to about 10,200 mg/l neomycin sulfate is used.

4. The medium of claim 1 wherein the gram-negative inhibitor is potassium tellurite.

5. The medium of claim 1 wherein about 0.98 to about 1.02 ml/l of 1% solution of potassium tellurite is used.

6. The medium of claim 1 wherein the nitrogen source comprises at least two peptones.

7. The medium of claim 6 wherein the peptones are Trypticase and Phytone.

8. A broth medium for the detection of Group D enterococci comprising per liter of medium:
    (a) about 13.5 to about 16.5 gm Trypticase,
    (b) about 4.5 to about 5.5 gm Phytone,
    (c) about 0.9 to about 1.1 gm esculin hydrolysate,
    (d) about 1.8 to about 2.2 gm sodium thioglycollate,
    (e) about 9800 to about 10,200 mg neomycin sulfate,
    (f) about 0.98 to about 1.02 ml potassium tellurite, (1% solution)
    (g) about 0.48 to about 0.52 gm ferric ammonium citrate, and
    (h) distilled water,
    (i) said medium having a pH of about 6.6.

9. A broth medium for the detection of Group D enterococci comprising per liter of medium:
    (a) 15.0 gm Trypticase,
    (b) 5.0 gm Phytone,
    (c) 1.0 gm esculin hydrolysate,
    (d) 2.0 gm sodium thioglycollate,
    (e) 10,000 mg neomycin sulfate,
    (f) 1.0 ml potassium tellurite (1% solution),
    (g) 0.5 gm ferric ammonium citrate, and
    (h) distilled water,
    (i) said medium having a pH of about 6.6.

* * * * *